US00PP15137P2

(12) United States Plant Patent
Freyre

(10) Patent No.: US PP15,137 P2
(45) Date of Patent: Sep. 7, 2004

(54) ANAGALLIS PLANT NAMED 'WILDCAT BLUE'

(50) Latin Name: *Anagallis monelli*
Varietal Denomination: Wildcat Blue

(75) Inventor: Rosanna Freyre, Durham, NH (US)

(73) Assignee: University of New Hampshire, Durham, NH (US)

( * ) Notice: Subject to any disclaimer, the term of this patent is extended or adjusted under 35 U.S.C. 154(b) by 0 days.

(21) Appl. No.: 10/721,990

(22) Filed: Nov. 25, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—W C Haas
(74) *Attorney, Agent, or Firm*—C. A. Whealy

(57) ABSTRACT

A new and distinct cultivar of Anagallis plant named 'Wildcat Blue', characterized by its compact and outwardly spreading plant habit; freely branching growth habit; numerous single flowers that are blue in color; and good garden performance.

1 Drawing Sheet

Botanical classification/cultivar designation: *Anagallis monelli* cultivar 'Wildcat Blue'.

BACKGROUND OF THE INVENTION

The present Invention relates to a new and distinct cultivar of Anagallis plant, botanically known as *Anagallis monelli,* and hereinafter referred to by the cultivar name 'Wildcat Blue'.

The new Anagallis is a product of a planned breeding program conducted by the Inventor in Durham, N.H. The objective of the breeding program is to create new compact Anagallis plants with freely and early flowering habit.

The new Anagallis originated from a cross-pollination made by the Inventor on Mar. 6, 2000, of a proprietary selection of *Anagallis monelli* identified as code number UNH 9-52-3, not patented, as the female, or seed parent, with a proprietary selection of *Anagallis monelli* identified as code number UNH 9-16-1, not patented, as the male, or pollen parent. The new Anagallis was selected as a single plant from the resulting progeny of the cross-pollination in Durham, N.H., on the basis of its plant habit and attractive flower coloration.

Asexual reproduction of the new cultivar by terminal vegetative cuttings since Sep. 21, 2000, taken in Durham, N.H. has shown that the unique features of this new Anagallis are stable and reproduced true to type in successive generations.

SUMMARY OF THE INVENTION

Plants of the cultivar 'Wildcat Blue' have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Wildcat Blue'. These characteristics in combination distinguish 'Wildcat Blue' as a new and distinct cultivar:

1. Compact and outwardly spreading plant habit.
2. Freely branching growth habit.

3. Numerous single flowers that are blue in color.
4. Good garden performance.

In side-by-side comparisons conducted in Durham, N.H., plants of the new Anagallis differed from plants of the female parent selection, in the following characteristics:

1. Plants of the new Anagallis were not as compact as plants of the female parent selection.
2. Plants of the new Anagallis had larger leaves than plants of the female parent selection.
3. Plants of the new Anagallis flowered earlier than plants of the female parent selection.

In side-by-side comparisons conducted at Durham, N.H., plants of the new Anagallis differed from plants of the male parent selection in the following characteristics:

1. Plants of the new Anagallis were more compact than and not as vigorous as plants of the male parent selection.
2. Plants of the new Anagallis had obovate-shaped petals whereas plants of the male parent selection had more rounded petals.

Plants of the new Anagallis can be compared to plants of the Anagallis cultivar Skylover Blue, not patented. In side-by-side comparisons conducted in Durham, N.H., plants of the new Anagallis differed from plants of the cultivar Skylover Blue in the following characteristics:

1. Plants of the new Anagallis were more compact than and not as vigorous as plants of the cultivar Skylover Blue.
2. Plants of the new Anagallis had shorter internodes than plants of the cultivar Skylover Blue.
3. Plants of the new Anagallis flowered about one week earlier than plants of the cultivar Skylover Blue.
4. Plants of the new Anagallis had darker blue-colored flowers than plants of the cultivar Skylover Blue.

BRIEF DESCRIPTION OF THE PHOTOGRAPHS

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Anagallis.

The photograph at the top of the sheet comprises a side perspective view of these typical plants of 'Wildcat Blue' grown in a container.

The photograph at the bottom of the sheet is a close-up view of typical flowers and leaves of 'Wildcat Blue'.

DETAILED BOTANICAL DESCRIPTION

The aforementioned photographs and following observations and measurements describe plants grown in Bonsall, Calif., in a polyethylene-covered greenhouse during the summer under full sun conditions with day temperatures ranging from about 18 to about 35° C. and night temperatures ranging from about 7 to about 18° C. After planting rooted cuttings, plants were grown for about four months in 20-cm containers with three plants per container. Color references are made to The Royal Horticultural Society Colour Chart, 1995 Edition, except where general terms of ordinary dictionary significance are used.

Botanical classification: *Anagallis monelli* cultivar Wildcat Blue.

Parentage:

*Female parent.*—Proprietary selection of *Anagallis monelli* identified as code number UNH 9-52-3, not patented.

*Male parent.*—Proprietary selection of *Anagallis monelli* identified as code number UNH 9-16-1, not patented.

Propagation:

*Type cutting.*—Terminal vegetative cuttings.

*Time to initiate roots, summer.*—About five days at 24° C.

*Time to initiate roots, winter.*—About seven days at 24° C.

*Time to develop roots, summer.*—About 20 days at 24° C.

*Time to develop roots, winter.*—About 25 days at 24° C.

*Root description.*—Fine fibrous; white, close to 155D, in color.

*Rooting habit.*—Freely branching.

Plant description:

*Form.*—Annual flowering plant; compact; initially upright, then semi-upright to outwardly spreading and trailing; uniformly mounded plant form. Freely branching habit with lateral branches potentially forming at very node.

*Plant height.*—About 23 cm.

*Plant diameter* (*area of spread*), *single plant.*—About 26 cm.

*Vigor.*—Moderately vigorous to vigorous; rapid growth rate.

*Lateral branches.*—Length: About 36 cm. Diameter: About 3 mm. Internode length: About 3 cm. Texture: Smooth, glabrous. Color: 144A.

*Foliage description.*—Arrangement: Opposite; towards terminals, in whorls of three or four; simple; sessile. Length: About 2.5 cm. Width: About 8 mm. Shape: Narrowly oblanceolate. Apex: Acute. Base: Truncate. Margin: Entire. Texture, upper and lower surfaces: Glabrous, smooth. Venation pattern: Pinnate, arcuate. Color: Developing leaves, upper surface: 137A. Developing leaves, lower surface: 137B. Fully expanded leaves, upper surface: 147A. Fully expanded leaves, lower surface: 147B. Venation, upper surface: 147A. Venation, lower surface: 147B.

Flower description:

*Flower type and habit.*—Single star-shaped flowers; flowers face mostly upward or outward; terminal or axillary; freely flowering habit, about 12 open flowers and about 18 flower buds per lateral branch at one time.

*Natural flowering season.*—Plants flower from April to October in the Northern Hemisphere until frost in the autumn; flowering continuous during this period. Plants start flowering about six to eight weeks after planting rooted cuttings. Flowers not persistent.

*Flower longevity on the plant.*—About four to five days.

*Fragrance.*—None detected.

*Flower size.*—Diameter: About 2.5 cm. Depth (height): About 8 mm.

*Flower buds.*—Length: About 1 cm. Diameter: About 3.5 mm. Shape: Ovate. Color: 99A.

*Petals.*—Quantity/arrangement: About five petals arranged in a single whorl. Length: About 1.3 cm. Width: About 1 cm. Shape: Obovate. Apex: Rounded. Base: Attenuate. Margin: Entire. Texture, upper and lower surfaces: Smooth, velvety. Color: When opening, upper surface: 99B. When opening, lower surface: 98A. Fully opened, upper surface: 99B to 99C; towards base, 59C. Fully opened, lower surface: 96B.

*Sepals.*—Arrangement/appearance: Five sepals arranged in a single whorl; star-shaped Length: About 8 mm. Width: About 2 mm. Shape: Lanceloate. Apex: Acute. Base: Truncate. Margin: Entire. Texture, upper and lower surfaces: Smooth, glabrous. Color, upper and lower surfaces: 137C.

*Peduncles.*—Length: About 3.5 cm. Width: Less than 1 mm. Angle: About 60 to 75° from the main stem, then more upright. Strength: Moderately strong. Texture: Smooth, glabrous. Color: 144A.

*Reproductive organs.*—Stamens: Quantity per flower: About five. Anther shape: Curved; sickle-shaped. Anther length: About 2 mm. Anther width: About 1 mm. Anther color: 12A. Pollen amount: Moderate. Pollen color: 12A. Pistils: Quantity per flower: One. Pistil length: About 7 mm. Style length: About 4 mm. Style color: 61C. Stigma shape: Rounded. Stigma color: 150A. Ovary color: 145C.

*Seed/fruit.*—Seed and/or fruit production has not been observed.

Disease/pest resistance: Plants of the new Anagallis have not been noted to be resistant to pathogens or pests common to Anagallis.

Garden performance: Plants of the new Anagallis have been observed to have good garden performance. Plants of the new Anagallis have been noted to tolerate temperatures from below 0 to 40° C. and have excellent tolerance to rain and wind.

What is claimed is:

1. A new and distinct cultivar of Anagallis plant named 'Wildcat Blue', as illustrated and described.

* * * * *

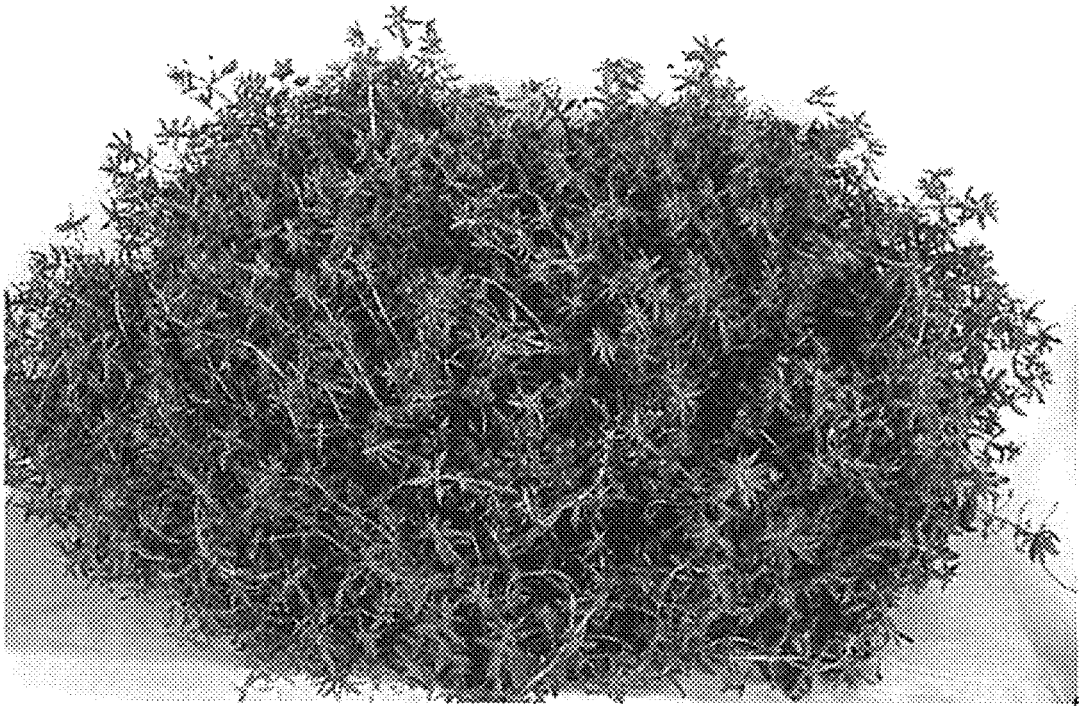
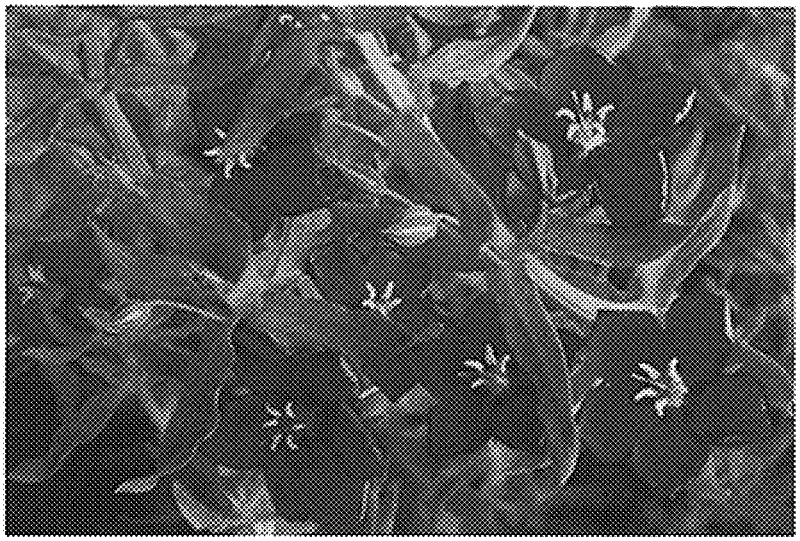

UNITED STATES PATENT AND TRADEMARK OFFICE

CERTIFICATE OF CORRECTION

PATENT NO. : PP 15,137 P2
DATED : September 7, 2004
INVENTOR(S) : Rosanna Freyre It is certified that error appears in the above-identified patent and that said Letters Patent is hereby corrected as shown below:

Column 1,
Line 3, the following statement of federal sponorship should be inserted
-- This invention was made with government support under USDA/CSREES Cooperative Agreement Number 01-90015-0420 awarded by the US Department of Agriculture Cooperative State Research, Education, and Extension Service. The government has certain rights in the invention. --

Signed and Sealed this

Twenty-sixth Day of April, 2005

JON W. DUDAS
*Director of the United States Patent and Trademark Office*